US012778905B2

(12) United States Patent
Kitayama et al.

(10) Patent No.: US 12,778,905 B2
(45) Date of Patent: Nov. 3, 2026

(54) CANCER CELL GROWTH INHIBITING COMPOSITION AND PROCESSED FOOD

(71) Applicants: HAGIHARA FARM PRODUCTION INSTITUTE CO., LTD., Nara (JP); KINKI UNIVERSITY, Osaka (JP)

(72) Inventors: Takashi Kitayama, Kyoto (JP); Gengo Kashiwazaki, Nara (JP); Kazuya Ashida, Kyoto (JP); Toshiharu Hashizume, Nara (JP)

(73) Assignees: HAGIHARA FARM PRODUCTION INSTITUTE CO., LTD., Nara (JP); KINKI UNIVERSITY, Osaka (JP)

( * ) Notice: Subject to any disclaimer, the term of this patent is extended or adjusted under 35 U.S.C. 154(b) by 365 days.

(21) Appl. No.: 18/282,572

(22) PCT Filed: Mar. 16, 2022

(86) PCT No.: PCT/JP2022/011959
§ 371 (c)(1),
(2) Date: Sep. 18, 2023

(87) PCT Pub. No.: WO2022/196731
PCT Pub. Date: Sep. 22, 2022

(65) Prior Publication Data

US 2024/0189258 A1 Jun. 13, 2024

(30) Foreign Application Priority Data

Mar. 19, 2021 (JP) ................................. 2021-045942

(51) Int. Cl.
*A61K 31/131* (2006.01)
*A61K 9/00* (2006.01)
(Continued)

(52) U.S. Cl.
CPC .......... *A61K 31/131* (2013.01); *A61K 9/0056* (2013.01); *A61K 31/14* (2013.01); *A61K 31/505* (2013.01); *A61P 35/00* (2018.01)

(58) Field of Classification Search
CPC ....... A23L 33/10; A61K 31/131; A61K 31/14; A61K 31/505; A61K 9/0056; A61P 35/00; A61P 35/02
See application file for complete search history.

(56) References Cited

U.S. PATENT DOCUMENTS

2005/0158329 A1* 7/2005 Ghosh .................. A61K 31/045 514/724
2015/0291649 A1 10/2015 Rosemeyer et al.
(Continued)

FOREIGN PATENT DOCUMENTS

| | | | |
|---|---|---|---|
| WO | 2014/048998 | A1 | 4/2014 |
| WO | 2017/131175 | A1 | 8/2017 |
| WO | 2020/171210 | A1 | 8/2020 |

OTHER PUBLICATIONS

Ashida et al., "Antiproliferative effects of phytol derivatives on human T-cell lymphoid cell line Jurkat cells," Proceedings of the 101st Annual Meeting of the Chemical Society of Japan, 2021.
(Continued)

*Primary Examiner* — Savitha M Rao
(74) *Attorney, Agent, or Firm* — Greenblum & Bernstein, P.L.C.

(57) ABSTRACT

Phytol contained in watermelon sprouts is known to have an antiproliferative effect on cancer cell. However, there has been a problem in that a high dose is required to exert the antiproliferative effect on cancer cell.
A cancer cell growth-inhibiting composition including a substance having structures represented by formulas (1) to (6) has a higher antiproliferative effect on cancer cell than phytol by order of one or more magnitudes. Further, it is expected that these substances do not affect normal cells similarly to phytol. Thus, they are expected to provide an anticancer drug with less side effects.

[Chemical formula 200]

(1)

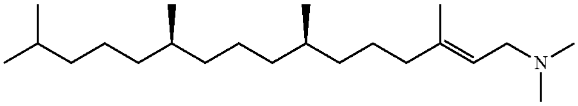

rac-PT21

[Chemical formula 201]

(2)

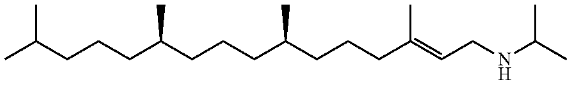

rac-PT22

[Chemical formula 202]

(3)

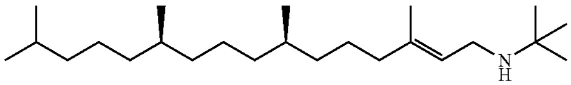

rac-PT23

[Chemical formula 203]

(4)

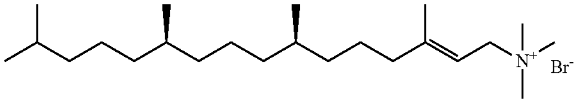

rac-PT26

(Continued)

-continued

[Chemical formula 204]

(5)

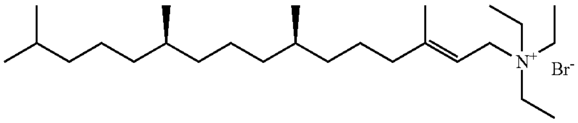

rac-PT27

[Chemical formula 205]

(6)

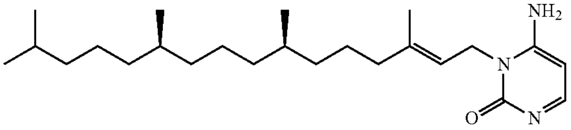

rac-PT28

16 Claims, No Drawings

(51) Int. Cl.

| | |
|---|---|
| ***A61K 31/14*** | (2006.01) |
| ***A61K 31/505*** | (2006.01) |
| ***A61P 35/00*** | (2006.01) |

(56) References Cited

U.S. PATENT DOCUMENTS

| | | | |
|---|---|---|---|
| 2019/0343909 | A1 | 11/2019 | Itoh et al. |
| 2022/0135514 | A1 | 5/2022 | Hashizume et al. |

OTHER PUBLICATIONS

Narender et al., "One-Pot Synthesis of Cationic Amphiphiles from n-Alcohols and Allyl Alcohols," *Synlett*, 2011, No. 12, pp. 1687-1692.

International Search Report issued Apr. 26, 2022 in PCT/JP2022/011959, with English translation thereof.

International Preliminary Report on Patentability issued Sep. 12, 2023, including Written Opinion dated Apr. 11, 2022, in PCT/JP2022/011959, with English translation thereof.

* cited by examiner

CANCER CELL GROWTH INHIBITING COMPOSITION AND PROCESSED FOOD

TECHNICAL FIELD

The present invention relates to a pharmaceutical composition and a processed food that include a phytol-based substance and have an antiproliferative effect on cancer cell.

BACKGROUND ART

It is known that a watermelon sprout extract has an antiproliferative effect on cancer cell (PTL 1). The literature disclosing this fact shows that phytol and lutein in the watermelon sprout extract exhibit this effect particularly well. Furthermore, since these substances do not affect normal cells, they are expected to provide an anticancer medical composition with less side effects.

CITATION LIST

Patent Literature

PTL 1: International Publication No. 2017/131175

SUMMARY OF INVENTION

Technical Problem

Phytol and lutein are expected to be used as an anticancer medical composition. However, there has been a problem in that a high dose is required to exert their effects.

Solution to Problem

The present invention has been conceived in view of the above-mentioned problems and provides a phytol-based substance that does not affect normal cells and that has a high antiproliferative effect on cancer cell.

More specifically, a cancer cell growth-inhibiting composition according to the present invention is characterized by including at least one selected from compounds having structures represented by formulas (1) to (6) and pharmaceutically acceptable salts thereof as an active ingredient.

[Chemical formula 1]

(1)

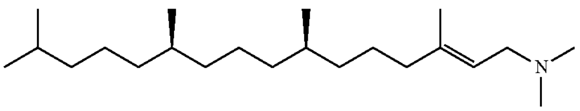

rac-PT21

[Chemical formula 2]

(2)

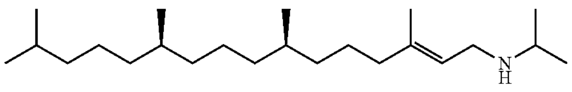

rac-PT22

-continued

[Chemical formula 3]

(3)

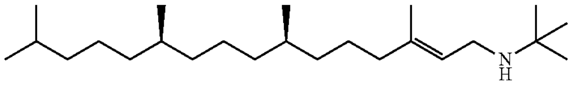

rac-PT23

[Chemical formula 4]

(4)

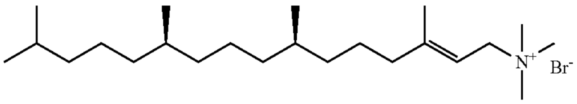

rac-PT26

[Chemical formula 5]

(5)

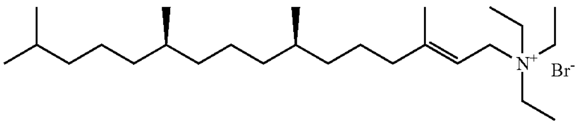

rac-PT27

[Chemical formula 6]

(6)

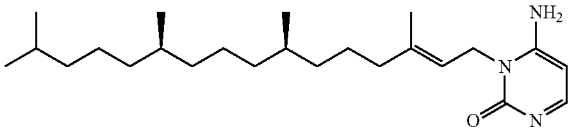

rac-PT28

Furthermore, the present invention can also be provided as a processed food. More specifically, the processed food according to the present invention is characterized by including at least one selected from compounds having structures represented by the formulas (1) to (6) and pharmaceutically acceptable salts thereof.

Note that “rac-PT21”, “rac-PT22”, “rac-PT23”, “rac-PT26”, “rac-PT27”, and “rac-PT28” in the formulas (1) to (6) are tentative names for each compound in the present specification, and they are not included in the structure itself of each compound.

Advantageous Effects of Invention

The cancer cell growth-inhibiting composition according to the present invention is expected to be able to inhibit the growth of cancer cells without causing side effects. Thus, it can be suitably used as an anticancer pharmaceutical composition. Furthermore, since the processed food according to the present invention includes the compound that has the antiproliferative effect on cancer cell, it is expected that cancer is prevented by taking the processed food regularly in the form of a supplement or the like.

DESCRIPTION OF EMBODIMENTS

Examples of the cancer cell growth-inhibiting composition and the processed food according to the present invention will be described below. Note that the following description is intended to illustrate an embodiment and an example of the present invention, and the present invention is not limited by the following description. The following description can be modified without departing from the scope of the present invention.

The cancer cell growth-inhibiting composition according to the present invention is configured by including at least one selected from phytol-based compounds of formulas (1) to (6) and pharmaceutically acceptable salts thereof as an active ingredient.

[Chemical formula 7]

(1)

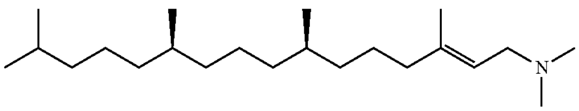

rac-PT21

[Chemical formula 8]

(2)

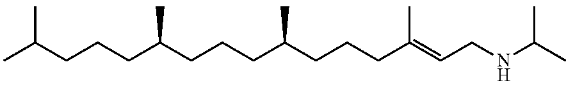

rac-PT22

[Chemical formula 9]

(3)

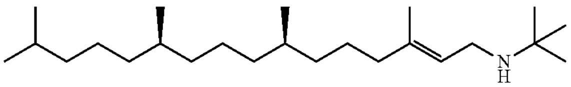

rac-PT23

[Chemical formula 10]

(4)

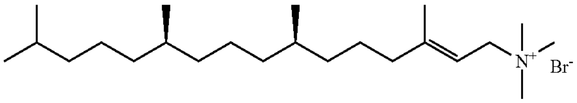

rac-PT26

[Chemical formula 11]

(5)

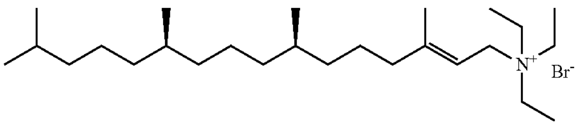

rac-PT27

[Chemical formula 12]

(6)

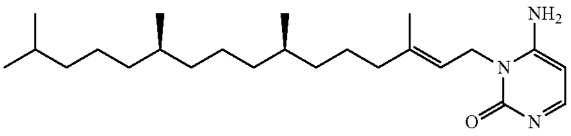

rac-PT28

The compound (rac-PT21) of the formula (1) is (7RS, 11RS,E)-1-N,N-dimethylamino-3,7,11,15-tetramethyl-2-hexadecene (dimethylamino phytol) (referred to as (7RS, 11RS,E)-1-N,N-dimethylamino-3,7,11,15-tetramethyl-2-hexadecene).

The compound (rac-PT22) of the formula (2) is (7RS, 11RS,E)-1-isopropylamino-3,7,11,15-tetramethyl-2-hexadecene (isopropylamino phytol) (referred to as (7RS,11RS, E)-1-isopropylamino-3,7,11,15-tetramethyl-2-hexadecene).

The compound (rac-PT23) of the formula (3) is (7RS, 11RS,E)-1-t-butylamino-3,7,11,15-tetramethyl-2-hexadecene (t-butylamino phytol) (referred to as (7RS,11RS,E)-1-t-butylamino-3,7,11,15-tetramethyl-2-hexadecene).

The compound (rac-PT26) of the formula (4) is (7RS, 11RS,E)-N,N,N-trimethyl-3,7,11,15-tetramethyl-2-hexadecenaminium bromide (trimethyl phytol ammonium bromide) (referred to as (7RS,11RS,E)-N,N,N-trimethyl-3,7,11, 15-tetramethyl-2-hexadeceneminium bromide).

The compound (rac-PT27) of the formula (5) is (7RS, 11RS,E)-N,N,N-triethyl-3,7,11,15-tetramethyl-2-hexadecenaminium bromide (triethyl phytol ammonium bromide) (referred to as (7RS,11RS,E)-N,N,N-triethyl-3,7,11,15-tetramethyl-2-hexadeceneminium bromide).

The compound (rac-PT28) of the formula (6) is 6-amino-1-((7R,11R,E)-3,7,11,15-tetramethyl-2-hexadecenyl)pyrimidin-2(1H)-one (cytosine phytol) (referred to as 6-amino-1-((7R,11R,E)-3,7,11,15-tetramethyl-2-hexadecenyl) pyrimidin-2(1H)-one).

When these compounds are used as the cancer cell growth-inhibiting composition (pharmaceutical composition), each compound can be used alone or as a salt by mixing the compound with a pharmaceutically acceptable acid in a solvent such as, for example, water, methanol, ethanol, or acetone. Examples of the pharmaceutically acceptable acid described herein include an inorganic acid such as hydrochloric acid, hydrobromic acid, a sulfuric acid, phosphoric acid, and nitric acid, and an organic acid such as acetic acid, propionic acid, oxalic acid, succinic acid, lactic acid, malic acid, tartaric acid, citric acid, maleic acid, fumaric acid, methanesulfonic acid, p-toluenesulfonic acid, and ascorbic acid.

The administration form of the pharmaceutical composition of the present invention is not particularly limited, and may be either oral or parenteral administration. Furthermore, the pharmaceutical composition can be made into an appropriate dosage form depending on the administration form. For example, the pharmaceutical composition can be prepared as various types of preparations such as an injection, an oral preparation such as a capsule, a tablet, a granule, a powder, a pill, or a fine granule, a rectal preparation, a lipophilic suppository, a hydrophilic suppository, or the like.

Furthermore, the cancer cell growth-inhibiting composition according to the present invention can be provided as a processed food. Examples of the processed food include not only general processed foods including favorite foods and health foods such as a candy, chewing gum, jelly, a biscuit, a cookie, a rice cracker, bread, a noodle, a fish/meat paste product, tea, a refreshing beverage, a coffee beverage, a milk beverage, a whey beverage, a lactic fermenting beverage, yogurt, ice cream, and pudding, but also foods with health claims such as foods for specified health uses and foods with nutrient function claims specified in the regulatory system "Foods with Health Claims" by the Ministry of Health, Labour, and Welfare, Japan. Further, a dietary supplement (a supplement), feed, a food additive, and the like are also included in the processed food.

The processed food according to the present invention can be prepared by adding the cancer cell growth-inhibiting composition to raw materials of these processed foods.

EXAMPLE

1. Synthesis of Compounds

Hereinafter, synthesis of compounds of the formulas (1) to (6) will be described.

<1-1> di

(7RS,11RS,E)-1-bromo-3,7,11,15-tetramethyl-2-hexadecene

Synthesis of (7RS,11RS,E)-1-bromo-3,7,11,15-tetramethyl-2-hexadecene

[Chemical Formula 13]

(7)

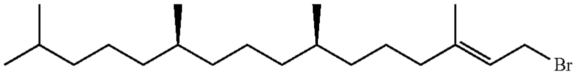

di

First, a compound of the formula (7) was synthesized. The "di" is a tentative name for the compound having a structure of the formula (7) in the present specification, and the "di" is not included in the structure itself of the compound of the formula (7).

To $Et_2O$ (diethyl ether) (5 mL) placed in a 100 mL two-necked flask, phytol (CAS number: 7541-49-3) (500 mg, 1.686 mmol) dissolved in $Et_2O$ (20 mL) was added, and the resulting mixture was stirred for a while being at 0° C. After that, phosphorus tribromide (0.064 mL, 0.674 mmol, 0.4 eq) was added dropwise, and the resulting mixture was stirred at the same temperature for 30 minutes.

The reaction was confirmed by TLC (Hexane/AcOEt (ethyl acetate)=5/1). After confirming on TLC that the raw materials had been used up, the reaction was stopped by adding a saturated aqueous solution of sodium bicarbonate dropwise. Extraction was performed with ethyl acetate, and an organic layer was collected. The organic layer was neutralized with a saturated aqueous solution of sodium bicarbonate, washed with brine, and then dried over anhydrous sodium sulfate. Sodium sulfate was removed by gravity filtration, and the remaining solution was concentrated under reduced pressure using a rotary evaporator to obtain 449.9 mg (74%) of a crude product in the form of reddish brown oil. No purification operations were performed.

The NMR spectrum of the product obtained by the above-described procedure is shown below.

Yield (74%: reddish brown oil) $^1$H NMR (400 MHz, $CDCl_3$): δ 5.53 (1H, t, J=8.4 Hz), 4.04 (2H, d, J=8.4 Hz), 2.02 (2H, t, J=7.6 Hz), 1.62-1.50 (2H, m), 1.72 (3H, d, J=1.3 Hz), 1.41-1.02 (21, m), 0.89-0.82 (14H, m). The obtained data was as described above.

From the above-described results, it was found that this product had the structure of the formula (7).

<1-2> PT21 Synthesis of (7RS,11RS,E)-1-N,N-dimethylamino-3,7,11,15-tetramethyl-2-hexadecene (PT21)

The "di" of the formula (7) (24.9 mg, 0.07 mmol) dissolved in $CH_2Cl_2$ (1.0 mL) was placed in a 5 mL screw tube and stirred at room temperature. After that, 50% dimethylamine (7 μL, 0.14 mmol, 2.0 eq) was added dropwise, and the resulting mixture was stirred at room temperature for 30 minutes.

Completion of the reaction was confirmed by TLC (Hexane/AcOEt=5/1), and the resulting mixture was diluted with water. Extraction was performed on the reaction solution three times with $CH_2Cl_2$, and the extract was washed three times with a saturated saline solution. The extract was then dried over anhydrous sodium sulfate, concentrated under reduced pressure using a rotary evaporator, and dried under vacuum. A product thus obtained was separated and purified by silica gel open column chromatography (AcOEt (Et3N: triethylamine 1%)) to obtain 9.1 mg (40%) of a yellow oily product PT21.

The NMR spectrum of the product PT21 is shown below.

Yield (26%: Yellow oil). IR (KBr): $^1$H NMR ($CDCl_3$, 500 MHz): δ=5.24 (1H, td, J=7.0, 1.2 Hz), 2.88 (2H, d, J=7.0 Hz), 2.22 (6H, s), 1.99 (2H, t, J=6.9 Hz), 1.63 (3H, s), 1.57-1.47 (1H, m), 1.47-1.32 (5H, m), 1.32-1.19 (8H, m), 1.19-1.10 (3H, m), 1.10-0.98 (4H, m), 0.90-0.80 (12H, m). $^{13}$C NMR ($CDCl_3$, 125 MHz): δ=138.8, 121.4, 57.0, 45.2, 40.1, 39.4, 37.4, 37.3, 37.2, 36.6, 32.8, 32.7, 27.9, 25.2, 24.8, 24.4, 22.7, 22.6, 19.8, 19.7, 16.2. HRMS m/z: [M+H]+ Calcd for $C_{22}H_{46}N$ 324.3630, found 324.3636. The obtained data was as described above.

From the above-described results, it was found that this product PT21 had the structure of the formula (1).

<1-3> PT22

Synthesis of (7RS,11RS,E)-1-isopropylamino-3,7,11,15-tetramethyl-2-hexadecene (PT22)

Isopropylamine (14.0 μL, 9.87 mg, 0.17 mmol, 2.0 eq) dissolved in $CH_2Cl_2$ (0.4 mL) was placed in a 5 mL screw tube and stirred at room temperature. After that, the "di" of the formula (7) (30.0 mg, 0.083 mmol) dissolved in $CH_2Cl_2$ (0.6 mL) was added dropwise over 10 minutes, and the resulting mixture was stirred at room temperature for 90 minutes. Completion of the reaction was confirmed by TLC (Hexane/AcOEt=5/1), and the resulting mixture was diluted with water. Extraction was performed on the reaction solution three times with $CH_2Cl_2$, and the extract was washed three times with a saturated saline solution. The extract was then dried over anhydrous sodium sulfate, concentrated under reduced pressure using a rotary evaporator, and then vacuum dried. A product thus obtained was separated and purified by silica gel open column chromatography (Hexane/AcOEt=3/1 and AcOEt (Et3N: triethylamine 1%)) to obtain 11.1 mg (40%) of a yellow oily product PT22.

The NMR spectrum of the product PT22 is shown below.

Yield (40%: Yellow oil). IR (KBr): $^1$H NMR ($CDCl_3$, 500 MHz): δ=5.25 (1H, td, J=6.8, 1.2 Hz), 3.21 (2H, d, J=6.7 Hz), 2.82 (1H, m), 1.96 (2H, br m), 1.63 (3H, s), 1.57-1.46 (1H, m), 1.46-1.31 (5H, m), 1.31-1.16 (9H, m), 1.16-1.11 (2H, m), 1.06 (10H, br, d, J=6.3 Hz), 0.89-0.81 (12H, m). $^{13}$C NMR ($CDCl_3$, 125 MHz): δ=137.6, 122.8, 48.2, 44.9, 39.9, 37.4, 37.3, 37.3, 37.2, 36.6, 32.7, 32.6, 27.9, 25.1, 24.7, 24.4, 22.9, 22.6, 19.8, 19.7, 16.1. HRMS m/z: [M+H]+ Calcd for $C_{23}H_{48}N$ 338.3787, found 338.3785. The obtained data was as described above. From the above-described results, it was found that this product PT22 had the structure of the formula (2).

<1-4> PT23

Synthesis of (7RS,11RS,E)-1-t-butylamino-3,7,11,15-tetramethyl-2-hexadecene (PT23)

Tert-butylamine (18.0 μL, 12.2 mg, 0.16 mmol, 2.0 eq) dissolved in $CH_2Cl_2$ (2.0 mL) was placed in a 5 mL screw tube and stirred at room temperature. After that, the "di" of the formula (7) (30.0 mg, 0.08 mmol) dissolved in $CH_2Cl_2$ (2.0 mL) was added dropwise over 10 minutes, and the resulting mixture was stirred at room temperature for 2.5 hours. Completion of the reaction was confirmed by TLC (Hexane/AcOEt=5/1), and the resulting mixture was diluted with water. Extraction was performed on the reaction solution three times with $CH_2Cl_2$, and the extract was washed three times with a saturated saline solution. The extract was then dried over anhydrous sodium sulfate, concentrated under reduced pressure using a rotary evaporator, and then vacuum dried. A product thus obtained was separated and purified by silica gel open column chromatography (Hexane/AcOEt=3/1 and AcOEt (triethylamine 1%)) to obtain 13.7 mg (49%) of a yellow oily product PT23.

The NMR spectrum of the product PT23 is shown below.

Yield (49%: Yellow oil). IR (KBr): $^1$H NMR ($CDCl_3$, 500 MHz): δ=5.26 (1H, td, J=6.8, 1.2 Hz), 3.18 (2H, d, J=6.8 Hz), 1.95 (2H, br, m), 1.63 (3H, s), 1.57-1.47 (1H, m), 1.47-1.32 (6H, m), 1.32-1.19 (10H, m), 1.19-1.10 (12H, m), 1.10-0.98 (5H, m), 0.90-0.80 (13H, m). $^{13}$C NMR ($CDCl_3$, 125 MHz): δ=137.7, 123.0, 50.4, 40.1, 39.9, 39.3, 37.4, 37.3, 37.3, 36.7, 32.8, 32.7, 28.9, 27.9, 25.2, 24.8, 24.4, 22.7, 22.6, 19.7, 19.7, 16.1. HRMS m/z: [M+H]+ Calcd for $C_{24}H_{50}N$ 352.3943, found 352.3946. The obtained data was as described above. From the above-described results, it was found that this product PT23 had the structure of the formula (3).

<1-5> PT26

Synthesis of (7RS,11RS,E)-N,N,N-trimethyl-3,7,11,15-tetramethyl-2-hexadecenaminium bromide (PT26)

The "di" of the formula (7) (70.0 mg, 0.2 mmol) dissolved in THF (2.1 mL) was placed in a 5 mL screw tube and stirred at room temperature. After that, Me3N (26.0 μL, 0.3 mmol, 1.5 eq) was added dropwise, and the resulting mixture was stirred at room temperature for 23 hours. The reaction progress was confirmed by TLC (Hexane/AcOEt=5/1), and Me3N (:trimethyltriamine, 26.0 μL, 0.3 mmol, 1.5 eq) was further added. After that, the resulting mixture was stirred for 4 hours (27 hours in total). Completion of the reaction was confirmed by TLC (Hexane/AcOEt=5/1). The reaction solution was concentrated under reduced pressure using a rotary evaporator. After AcOEt was added to the reaction solution, the reaction solution was subjected to suction filtration to obtain 37.7 mg (45%) of a white solid PT26.

The NMR spectrum of the product PT26 is shown below.

Yield (45%: white solid). Mp: 199-201° C. IR (KBr): $^1$H NMR ($CDCl_3$, 400 MHz): δ=5.34 (1H, t, J=7.8 Hz), 4.27 (2H, d, J=8.2 Hz), 3.41 (9H, s), 2.12 (2H, br, m), 1.90 (3H, s), 1.76 (1H, s), 1.58-1.48 (1H, m), 1.48-1.33 (4H, m), 1.33-1.19 (7H, m), 1.19-0.99 (7H, m), 0.91-0.80 (12H, m). $^{13}$C NMR ($CDCl_3$, 100 MHz): δ=153.6, 110.0, 63.9, 52.4, 40.5, 39.3, 37.4, 37.3, 37.2, 36.7, 32.7, 32.6, 27.9, 25.2, 24.7, 24.4, 22.7, 22.6, 19.7, 19.6, 17.7. HRMS m/z: [M+H]+ Calcd for $C_{23}H_{48}N$ 338.3787, found 338.3787. The obtained data was as described above. From the above-described results, it was found that this product PT26 had the structure of the formula (4).

<1-6> PT27

Synthesis of (7RS,11RS,E)-N,N,N-triethyl-3,7,11,15-tetramethyl-2-hexadecenaminium bromide (PT27)

The "di" of the formula (7) (50.0 mg, 0.14 mmol) dissolved in THF (1.5 mL) was placed in a 5 mL screw tube and stirred at room temperature. After that, Et3N (60.0 μL, 0.42 mmol, 3.0 eq) was added dropwise, and the resulting mixture was stirred at room temperature for 7 hours. Completion of the reaction was confirmed by TLC (Hexane/AcOEt=5/1). After Et2O was added to the reaction solution, the reaction solution was subjected to suction filtration to obtain 32.0 mg (50%) of a white solid PT27.

The NMR spectrum of the product PT27 is shown below.

Yield (50%: white solid). Mp: 132-135° C. IR (KBr): $^1$H NMR ($CDCl_3$, 400 MHz): δ=5.19 (1H, td, J=7.7, 1.0 Hz), 4.08 (2H, d, J=7.7 Hz), 3.47 (6H, q, J=7.3 Hz), 2.10 (2H, br, m), 1.85 (3H, s), 1.66 (2H, s), 1.58-1.48 (1H, m), 1.43 (11H, br, t, J=7.3 Hz), 1.39-1.31 (3H, m), 1.31-1.17 (7H, m), 1.17-1.11 (2H, m), 1.11-0.98 (4H, m), 0.91-0.80 (12H, m). $^{13}$C NMR ($CDCl_3$, 100 MHz): δ=151.8, 109.3, 56.2, 53.1, 40.6, 39.3, 37.4, 37.3, 37.2, 36.7, 32.8, 32.6, 27.9, 25.2, 24.8, 24.4, 22.7, 22.6, 19.7, 19.6, 17.5, 8.3. HRMS m/z: [M+H]+ Calcd for $C_{26}H_{54}N$ 380.4256, found 380.4249. The obtained data was as described above. From the above-described results, it was found that this product PT27 had the structure of the formula (5).

<1-7> PT28

Synthesis of 6-amino-1-((7R,11R,E)-3,7,11,15-tetramethyl-2-hexadecenyl)pyrimidin-2(1H)-one (PT28)

Cytosine (184.4 mg, 1.66 mmol, 2.0 eq) dissolved in DMSO (10.0 mL) was placed in a 50 mL screw tube and stirred at room temperature. After that, the "di" of the formula (7) (297.5 mg, 0.83 mmol) was dissolved in DMSO (15.0 mL) and added dropwise over 15 minutes, and the resulting mixture was stirred at room temperature for 1 hour. Extraction was performed on the reaction solution with Hexane/AcOEt=4/1. Completion of the reaction was confirmed by TLC (Hexane/AcOEt=5/1). Extraction was performed on the reaction solution twice with AcOEt and $H_2O$. After being further washed with $H_2O$, the extract was dried over anhydrous sodium sulfate, concentrated under reduced pressure using a rotary evaporator, and then vacuum dried. A product thus obtained was separated and purified by silica gel open column chromatography (AcOEt/MeOH (methanol)=5/1) to obtain 59.5 mg (18%) of a pale yellow solid PT28.

The NMR spectrum of the product PT28 is shown below.

Yield (18%: pale yellow solid). Mp: 101-102° C. IR (KBr): 3348, 2955, 2928, 1639, 1578, 1547,1462, 1381, 1327, 1292, 1150, 1072, 868, 791, 567 cm-1. $^1$H NMR ($CDCl_3$, 500 MHz): δ 7.11 (1H, s), 5.66 (1H, d, J=7.1 Hz), 5.20 (1H, td, J=6.3, 0.9 Hz), 4.66 (2H, d, J=6.3 Hz), 2.03-1.98 (2H, m), 1.78 (3H, s), 1.56-1.49 (1H, m), 1.47-1.33 (5H, m), 1.32-1.18 (8H, m), 1.17-1.10 (3H, m), 1.10-0.99 (4H, m), 0.91-0.76 (13H, m). $^{13}$C NMR ($CDCl_3$, 125 MHz): δ 158.2, 153.0, 141.1, 117.5, 98.2, 41.0, 40.3, 39.9, 39.4, 37.4, 37.4, 37.3, 36.8, 32.8, 32.7, 28.0, 25.2, 24.8, 24.5, 22.8, 22.7, 19.8, 19.7, 16.6. HRMS m/z: [M+Na]+ Calcd for $C_{24}H_{43}N_3ONa$ 412.3304; Found 412.3306. The obtained data was as described above. From the above-described results, it was found that this product PT28 had the structure of the formula (6).

2. Evaluation of Growth Inhibiting Activity of Compounds for Human Leukemia T Cell Line Jurkat Cells The cancer cell growth-inhibiting activity of each sample described above was examined using Jurkat cells, which are from a human leukemia T cell line.

In each well of a 96-well plate, 50 μL of a Jurkat cell suspension prepared at $1\times10^5$ cells/mL was seeded. A DMSO solution of the evaluation sample was diluted 500 times with the culture medium. Immediately after that, 50 μL of the diluted sample solution was added to the cells to start a cell treatment. After the samples were stirred for 30 seconds using a microplate reader, the cells were cultured in an incubator. After 72 hours, 10 μL of Cell Count Reagent SF was added to each well. After a color reaction was performed in the incubator for 2 to 3 hours, the absorbance at 450 nm and 630 nm was measured using a microplate reader. Cell viability was determined using the following formula (F1).

$$\text{Cell viability (\%)}=[(As-Ab)/(Ac-Ab)]\times100 \quad \text{(F1)}$$

Note that As, Ab, and Ac are as follows.

As: absorbance of evaluation well

Ab: absorbance of negative control well

Ac: absorbance of control well

All the "absorbance" values in the above-described formula were calculated by subtracting the absorbance at 630 nm (referred to as $A_{630}$) from the absorbance at 450 nm (referred to as $A_{450}$), that is, "$A_{450}$-$A_{630}$". Further, $IC_{50}$ was calculated by linear approximation on a logarithmic graph using two concentrations that most tightly enclose the 50% cell viability point. The results are shown in Table 1.

TABLE 1

| compound | $IC_{50}$(μM) |
|---|---|
| 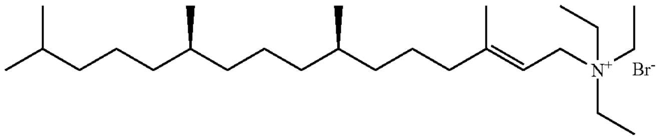 rac-PT27 | 0.48 |
| 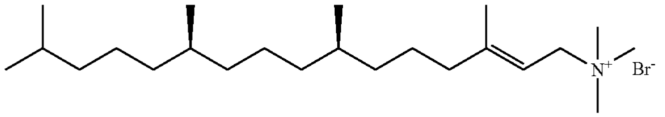 rac-PT26 | 1.41 |
| 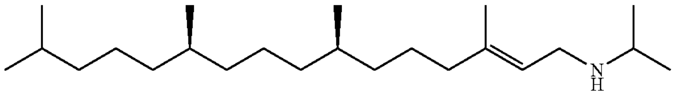 rac-PT22 | 2.6 |
| 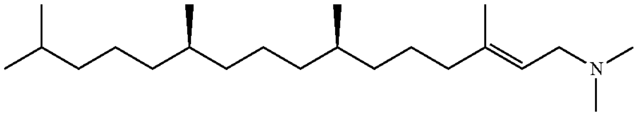 rac-PT21 | 2.8 |
| 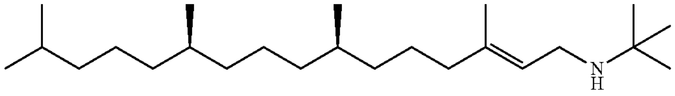 rac-PT23 | 3.1 |
| 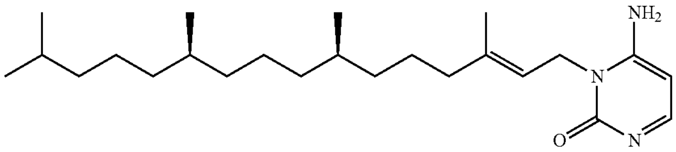 rac-PT28 | 3.2 |

TABLE 1-continued

| compound | $IC_{50}$(μM) |
|---|---|
| 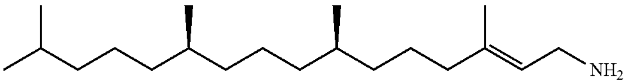<br>rac-PT10 | 3.8 |
| 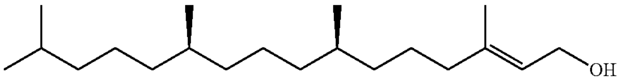<br>rac-PT0 | 29.8 |

Table 1 shows the structural formula and $IC_{50}$ value (μM) of each sample. As a reference, phytol (rac-PT0) and amino phytol (rac-PT10) ((7R,11R,E)-1-amino-3,7,11,15-tetramethyl-2-hexadecene) were also measured at the same time.

As a result, phytol (rac-PT0) was 29.8 μM, and amino phytol (rac-PT10) was 3.8 μM.

On the other hand, cytosine phytol (PT28) was 3.2 μM, and t-butylamino phytol (PT23) was 3.1 μM.

Furthermore, dimethylamino phytol (PT21) was 2.8 μM, and isopropylamino phytol (PT22) was 2.6 μM.

Furthermore, trimethyl phytol ammonium bromide (PT26) was 1.41 μM, and triethyl phytol ammonium bromide (PT27) was 0.48 μM.

That is, these six compounds according to the present invention were found to be more effective than phytol by an order of one to two magnitudes or more.

INDUSTRIAL APPLICABILITY

The cancer cell growth-inhibiting composition according to the present invention can be suitably used for the treatment and prevention of cancer.

The invention claimed is:

1. A cancer cell growth-inhibiting composition comprising at least one selected from compounds having structures represented by formulas (1) to (6) and pharmaceutically acceptable salts thereof as an active ingredient:

(1)

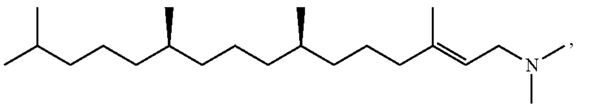

rac-PT21

(2)

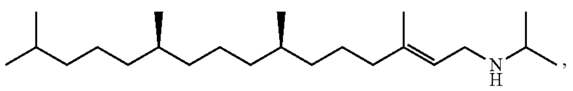

rac-PT22

(3)

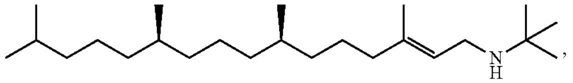

rac-PT23

-continued (4)

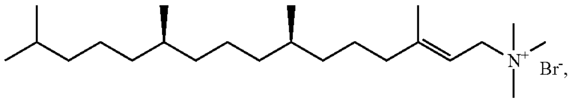

rac-PT26

(5)

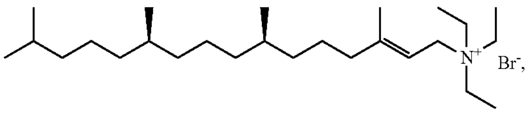

and rac-PT27

(6)

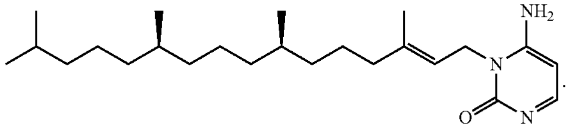

rac-PT28

2. A processed food comprising at least one selected from compounds having structures represented by formulas (1) to (6) and pharmaceutically acceptable salts thereof:

(1)

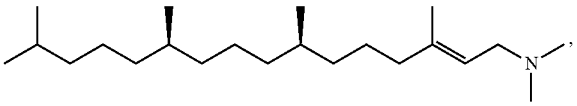

rac-PT21

(2)

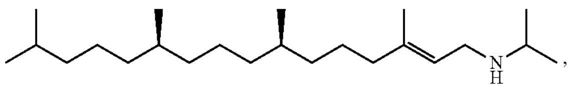

rac-PT22

(3)

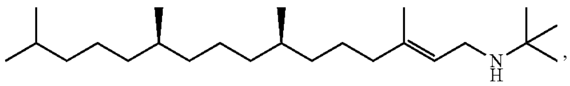

rac-PT23

-continued (4)

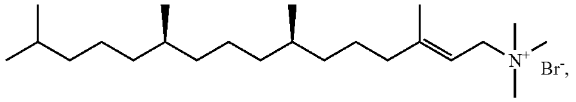

rac-PT26

(5)

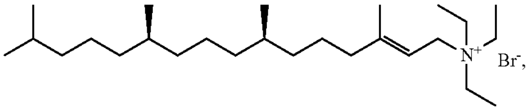

and rac-PT27

(6)

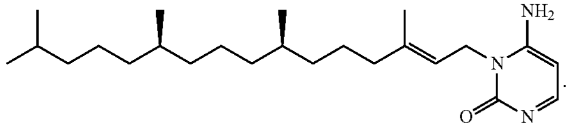

rac-PT28

3. The cancer cell growth-inhibiting composition of claim 1, wherein the composition comprises at least one selected from compounds having structures represented by formulas (1), (4), (5), and (6) and pharmaceutically acceptable salts thereof as an active ingredient.

4. The cancer cell growth-inhibiting composition of claim 1, wherein the composition comprises at least one selected from a compound having the structure represented by formula (1) and a pharmaceutically acceptable salt thereof as an active ingredient.

5. The cancer cell growth-inhibiting composition of claim 1, wherein the composition comprises at least one selected from a compound having the structure represented by formula (2) and a pharmaceutically acceptable salt thereof as an active ingredient.

6. The cancer cell growth-inhibiting composition of claim 1, wherein the composition comprises at least one selected from a compound having the structure represented by formula (3) and a pharmaceutically acceptable salt thereof as an active ingredient.

7. The cancer cell growth-inhibiting composition of claim 1, wherein the composition comprises at least one selected from a compound having the structure represented by formula (4) and a pharmaceutically acceptable salt thereof as an active ingredient.

8. The cancer cell growth-inhibiting composition of claim 1, wherein the composition comprises at least one selected from a compound having the structure represented by formula (5) and a pharmaceutically acceptable salt thereof as an active ingredient.

9. The cancer cell growth-inhibiting composition of claim 1, wherein the composition comprises at least one selected from a compound having the structure represented by formula (6) and a pharmaceutically acceptable salt thereof as an active ingredient.

10. The processed food of claim 2, wherein the processed food comprises at least one selected from compounds having structures represented by formulas (1), (4), (5), and (6) and pharmaceutically acceptable salts thereof as an active ingredient.

11. The processed food of claim 2, wherein the processed food comprises at least one selected from a compound having the structure represented by formula (1) and a pharmaceutically acceptable salt thereof as an active ingredient.

12. The processed food of claim 2, wherein the processed food comprises at least one selected from a compound having the structure represented by formula (2) and a pharmaceutically acceptable salt thereof as an active ingredient.

13. The processed food of claim 2, wherein the processed food comprises at least one selected from a compound having the structure represented by formula (3) and a pharmaceutically acceptable salt thereof as an active ingredient.

14. The processed food of claim 2, wherein the processed food comprises at least one selected from a compound having the structure represented by formula (4) and a pharmaceutically acceptable salt thereof as an active ingredient.

15. The processed food of claim 2, wherein the processed food comprises at least one selected from a compound having the structure represented by formula (5) and a pharmaceutically acceptable salt thereof as an active ingredient.

16. The processed food of claim 2, wherein the processed food comprises at least one selected from a compound having the structure represented by formula (6) and a pharmaceutically acceptable salt thereof as an active ingredient.

* * * * *